(12) United States Patent
Bachmann et al.

(10) Patent No.: US 10,806,488 B2
(45) Date of Patent: Oct. 20, 2020

(54) WORKING SLEEVE FOR A TROCAR

(71) Applicants: Karl-Heinz Bachmann, Villingendorf (DE); Thomas Gaiselmann, Villingendorf (DE); Siegfried Riek, Rottweil (DE)

(72) Inventors: Karl-Heinz Bachmann, Villingendorf (DE); Thomas Gaiselmann, Villingendorf (DE); Siegfried Riek, Rottweil (DE)

( * ) Notice: Subject to any disclaimer, the term of this patent is extended or adjusted under 35 U.S.C. 154(b) by 198 days.

(21) Appl. No.: 15/779,795

(22) PCT Filed: Nov. 8, 2016

(86) PCT No.: PCT/EP2016/076929
§ 371 (c)(1),
(2) Date: May 29, 2018

(87) PCT Pub. No.: WO2017/092976
PCT Pub. Date: Jun. 8, 2017

(65) Prior Publication Data
US 2018/0338775 A1 Nov. 29, 2018

(30) Foreign Application Priority Data
Nov. 30, 2015 (DE) .......................... 10 2015 120 776

(51) Int. Cl.
*A61B 17/34* (2006.01)
*A61B 17/29* (2006.01)

(52) U.S. Cl.
CPC .. *A61B 17/3421* (2013.01); *A61B 2017/2905* (2013.01); *A61B 2017/3435* (2013.01);
(Continued)

(58) Field of Classification Search
CPC ............ A61B 17/3415; A61B 17/3445; A61B 17/3447; A61B 17/3423; A61M 25/0026; A61M 2025/0037; A61M 2025/004
See application file for complete search history.

(56) References Cited

U.S. PATENT DOCUMENTS

| 9,687,270 B2 | 6/2017 | Gaiselmann et al. |
| 2005/0077689 A1 | 4/2005 | Hueil |

(Continued)

FOREIGN PATENT DOCUMENTS

| DE | 20110491 | 10/2001 |
| DE | 102007040358 | 3/2009 |

(Continued)

OTHER PUBLICATIONS

German Patent Office, "Office Action" issued in German patent application No. 10 2015 120 776.1, dated Aug. 3, 2016, document of 5 pages.

(Continued)

*Primary Examiner* — Wade Miles
*Assistant Examiner* — Mohammed S Adam
(74) *Attorney, Agent, or Firm* — Akerman LLP; Peter A. Chiabotti (57) ABSTRACT

A trocar system with a trocar which has a trocar mandrel, a trocar sleeve and a valve block, characterized by a tubular working sleeve having an axially continuous inner channel, in which the trocar can be inserted in such a way that the trocar sleeve is sealed with the outer perimeter thereof in the inner channel, so that the distal tip of the trocar mandrel projects distally out of the working sleeve and that the valve block is located proximally outside the inner channel, and having at least one working channel which is formed on the working sleeve and extends from a proximal inlet opening to a distal outlet opening.

20 Claims, 8 Drawing Sheets

(52) U.S. Cl.
CPC .............. *A61B 2017/3445* (2013.01); *A61B 2017/3447* (2013.01)

(56) References Cited

U.S. PATENT DOCUMENTS

| | | |
|---|---|---|
| 2007/0299387 A1 | 12/2007 | Williams et al. |
| 2008/0294184 A1 | 11/2008 | Smith |
| 2010/0280368 A1 | 11/2010 | Can et al. |
| 2015/0038792 A1 | 5/2015 | Gaiselmann et al. |

FOREIGN PATENT DOCUMENTS

| | | |
|---|---|---|
| DE | 102009012185 | 9/2010 |
| DE | 102012203908 | 6/2013 |
| DE | 102012203907 | 9/2013 |
| EP | 1520539 | 4/2005 |
| EP | 2179700 | 4/2010 |
| WO | 9219146 | 11/1992 |
| WO | 2013135354 | 9/2013 |

OTHER PUBLICATIONS

Patent Cooperation Treaty, "International Search Report," and English translation thereof issued in International Application No. PCT/EP2016/076929, document of 4 pages, dated Jan. 20, 2017.

WORKING SLEEVE FOR A TROCAR

CROSS REFERENCE TO RELATED APPLICATIONS

This application is a § 371 National Phase of PCT/EP2016/076929, filed Nov. 8, 2016, the entirety of which is herein incorporated by reference and which claims priority to German Patent Application No. 10 2015 120 776.1, filed Nov. 30, 2015.

BACKGROUND

The application relates to a trocar system.

SUMMARY

Trocars are used for minimally invasive endoscopic surgery. The trocars are used to create access to the intracorporeal surgical field. The trocar has a trocar mandrel, also known as an obturator. The trocar mandrel has a distal tip used for penetrating the tissue. On the trocar mandrel the trocar sleeve, which is punched through the tissue along with the trocar mandrel. As soon as the trocar tip has reached the surgical field, the trocar mandrel is withdrawn, whale the trocar sleeve remains as access for the surgery. At the proximal end of the trocar is a valve block, which especially serves for closing off the trocar sleeve following withdrawal of the trocar mandrel to prevent escape of an insufflation gas and to allow sealed introduction of an instrument, an endoscope or the like through the trocar sleeve.

Trocars of this type are known in many designs. For example, reference is made to EP 2 179 700 B1 or a corresponding trocar sold by the Ethicon Company under the brand name "ENDOPATH XCEL."

It is also known that working channels may be formed in the trocar sleeve, through which miniature instruments can be passed to the distal tip of the trocar or instruments located at the tip of the trocar can be operated (US 2008/0294184 A1, DE 10 2012 203 907 A1). In these trocars, separate formation of the trocar sleeve is necessary. This makes the trocar costly to manufacture. For use in surgery, different designs of trocar must be available.

The present disclosure provides a trocar system which makes it possible to provide any desired standardized trocars, with working channels for introduction of miniature instruments and the like, in a simple, cost-effective manner.

The present application provides a trocar system having the features and structures recited herein or with a working sleeve for such a trocar system.

Advantageous embodiments of the of the disclosure are described further in the structures and features recited herein.

The application is directed to trocar, consisting of a trocar mandrel, trocar sleeve and valve block, another working sleeve which has one or more working channels. The working sleeve is slid onto the trocar, where it coaxially surrounds the trocar manual and the trocar sleeve. The tip of the trocar, especially the penetrating distal tip of the trocar mandrel, projects distally out of the working sleeve. With the aid of the trocar and its distal tip, the working sleeve sitting on the trocar can also penetrate into the patient's body tissue, whereupon miniature instruments can be introduced through the working channels to perform dissection tasks at the trocar tip and especially also distally in front of the trocar tip. The valve block of the trocar in this process remains proximally outside of the inner channel of the working sleeve, so that the working sleeve can be used regardless of the respective specific form of the valve block.

The working sleeve is an accessory of simple design, which can be manufactured inexpensively and preferably from plastic. Large numbers of the working sleeves can be kept in stock in a few standard sizes corresponding to the external diameters and the axial lengths of the usual trocars, which simplifies purchasing and stocking especially in hospitals and makes it less expensive.

In an advantageous embodiment, the working sleeve is expanded in the form of a cage at its proximal end. This cage widens out proximally at the inlet end of the inner channel and is open in the proximal direction. This cage is used for accommodating the valve block of the trocar used in the working sleeve. The inlet opening of the working channel or working channels is located at the proximal edge of this cage, so that these inlet openings are freely accessible and allow easy introduction and manipulation of miniature instruments past the valve block.

In addition, means may be provided on the cage to allow fixation of the working sleeve, for example, on the arm of a stand or the like. Through fixation of the working sleeve, the trocar that can be positioned in the working sleeve is simultaneously fixed. The trocar sleeve remaining after removal of the trocar mandrel to provide access, for surgery is thus also fixed in its position and need not be held by the surgeon or assistants.

If an optical system is introduced into the trocar sleeve to observe the surgical field after removal of the trocar mandrel, means are preferably provided for fixing the optical system in the trocar sleeve. These means can be provided on the cage of the working sleeve or in the valve block of the trocar sleeve. Such means may fix the optical system by clamping, tensioning or using notches.

BRIEF DESCRIPTION

In the following, the features and structures of the present application will be explained in greater detail based on the embodiments shown in the drawings. These show the following.

BRIEF DESCRIPTION OF THE DRAWINGS

Figure 1:
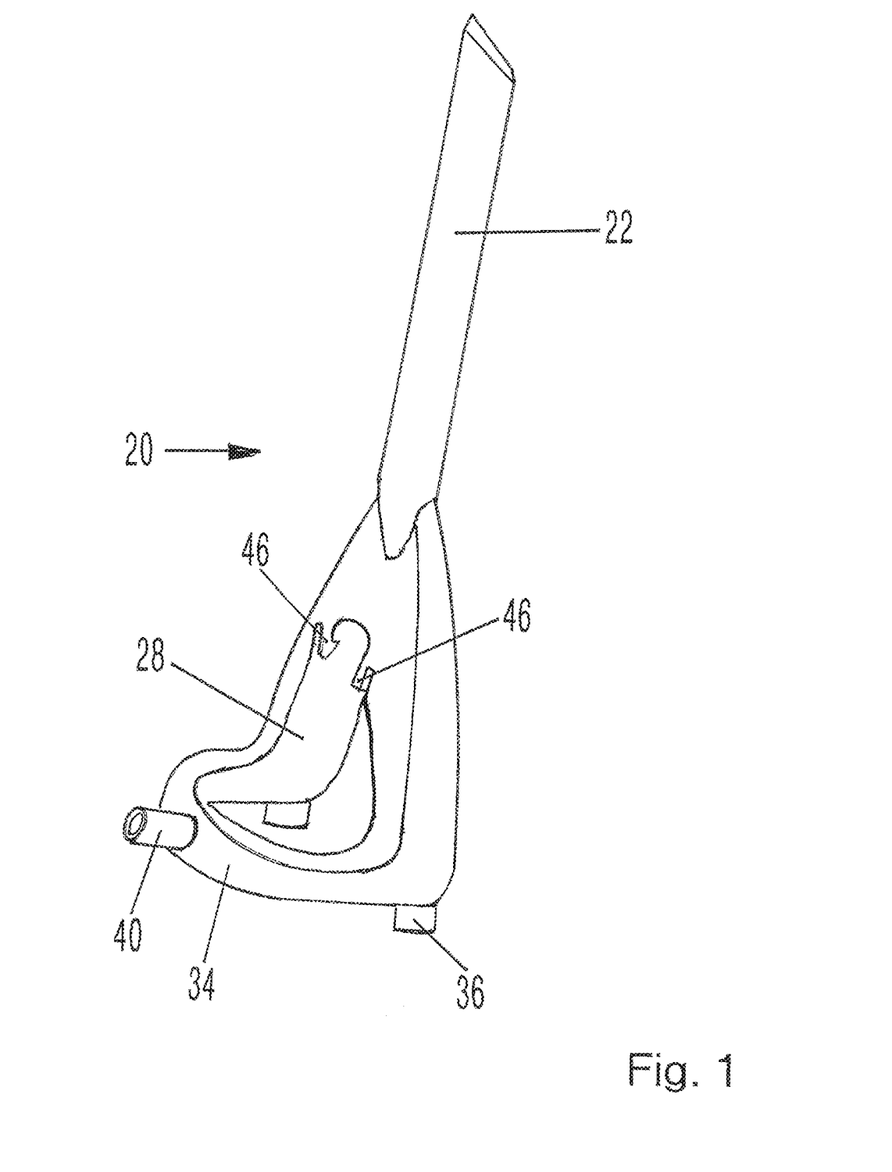
FIG. 1 a perspective view of the working sleeve according to the application in a first embodiment, FIG. 2 a side view of the working sleeve, FIG. 3 a side view of the working sleeve rotated through 90° relative to FIG. 2, FIG. 4 a front view of the distal end of the working sleeve, FIG. 5 a from view of the proximal end of the working sleeve, FIG. 6 cross-section along line A-A in FIG. 2, FIG. 7 a perspective view of a trocar according to the prior art for the trocar system according to the application and FIG. 8 a second embodiment of the working sleeve.
Figure 2:
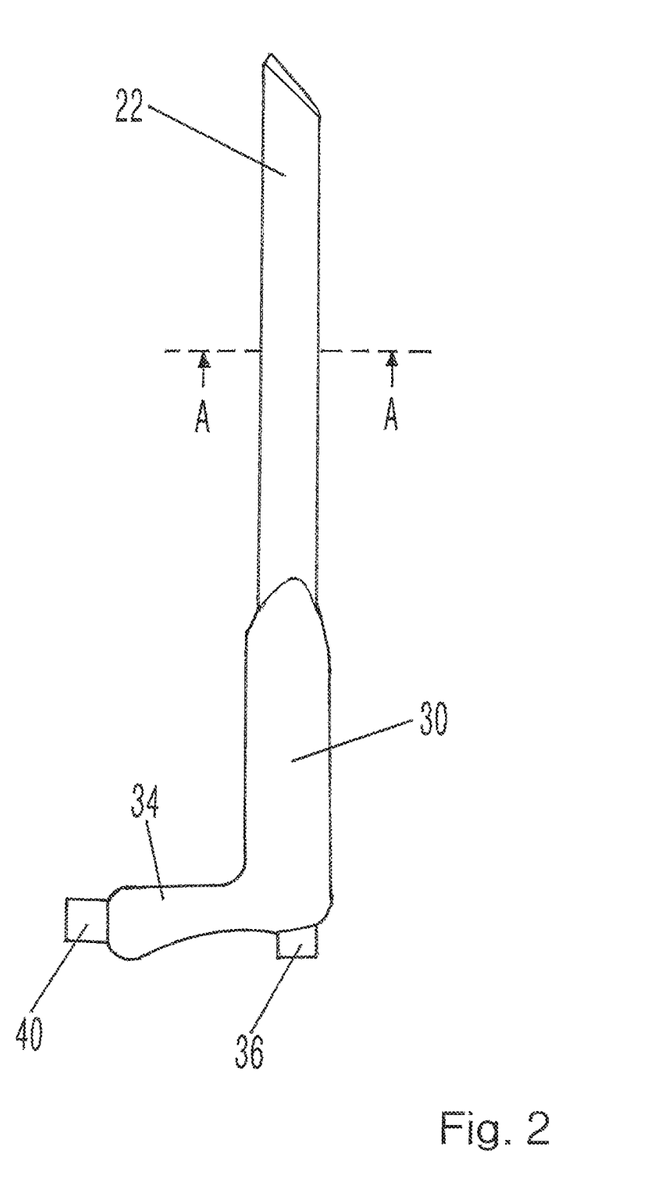
Figure 3:
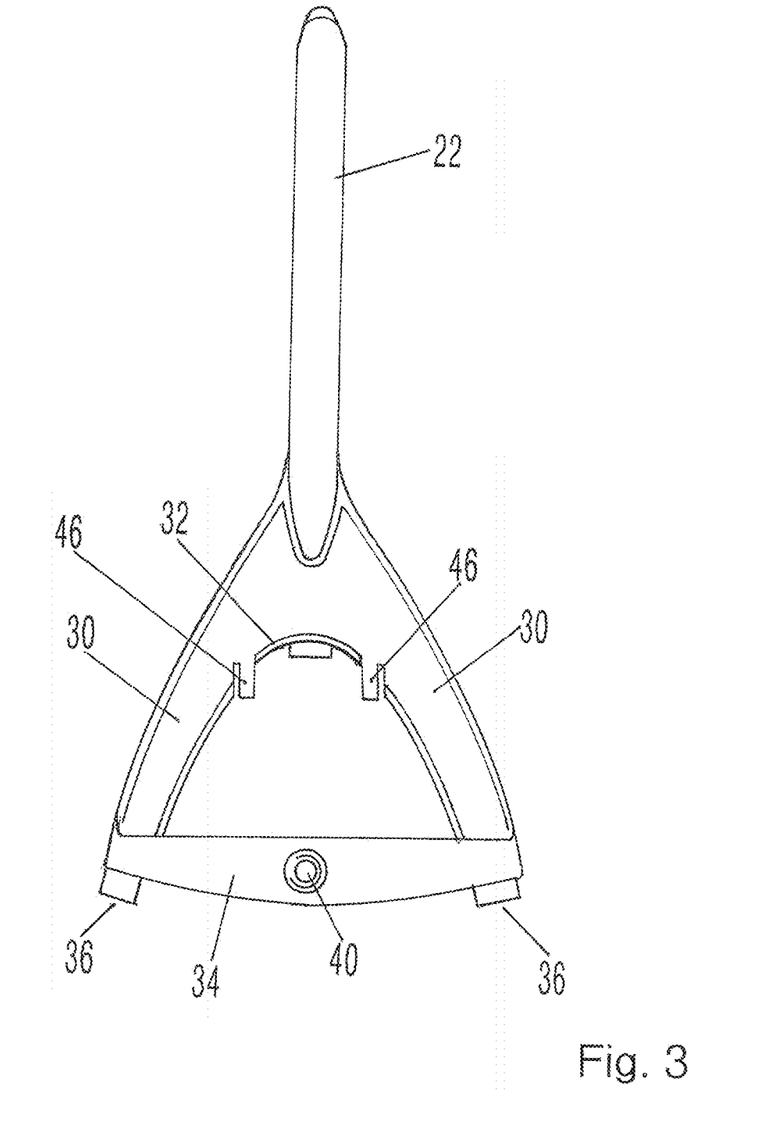
Figure 4:
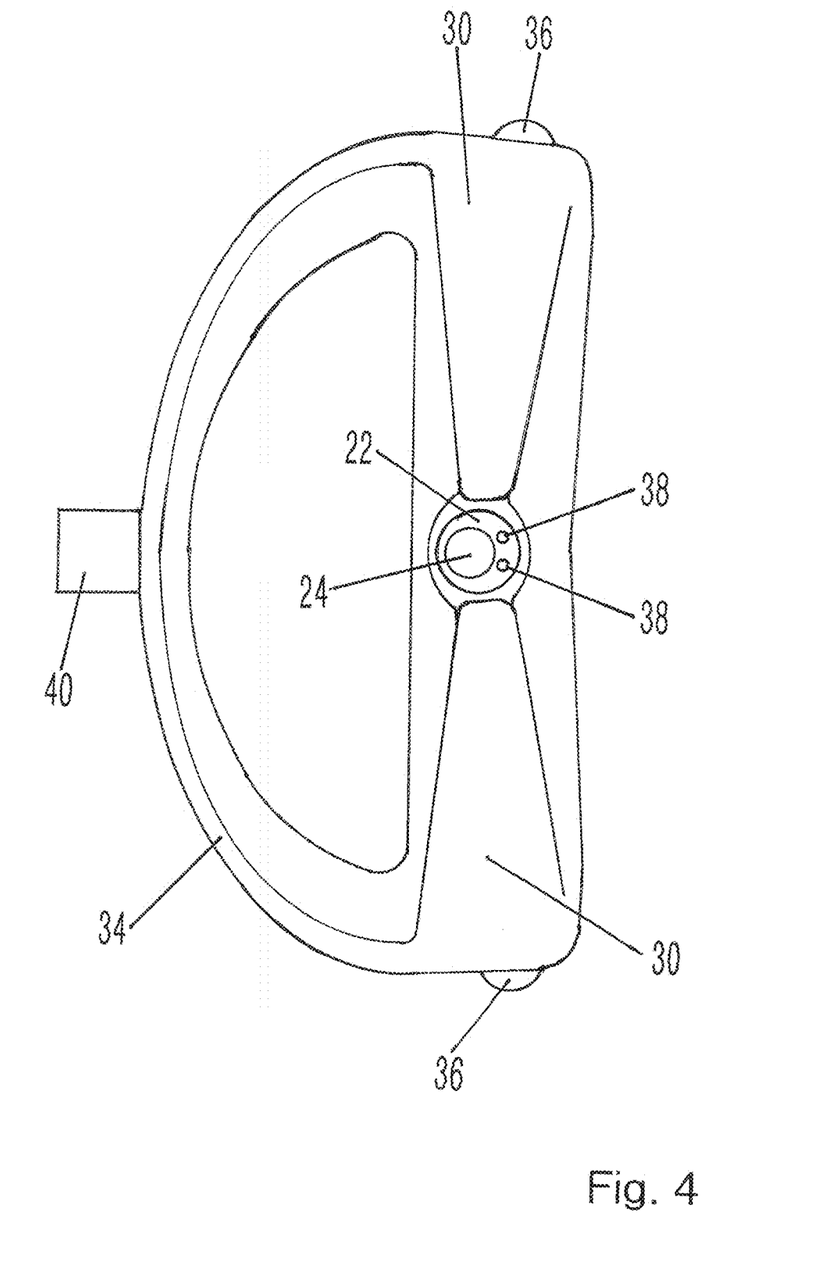
Figure 5:
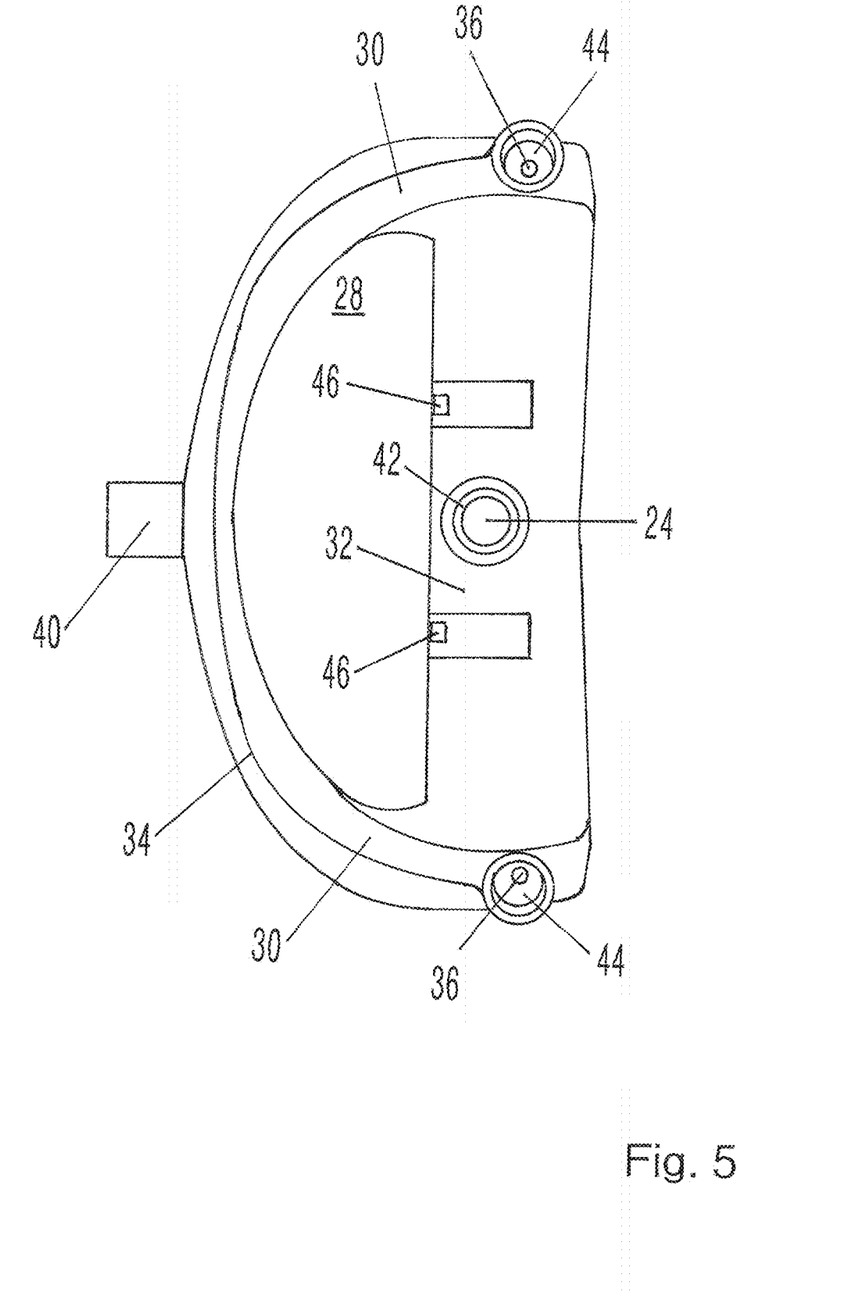
Figure 6:
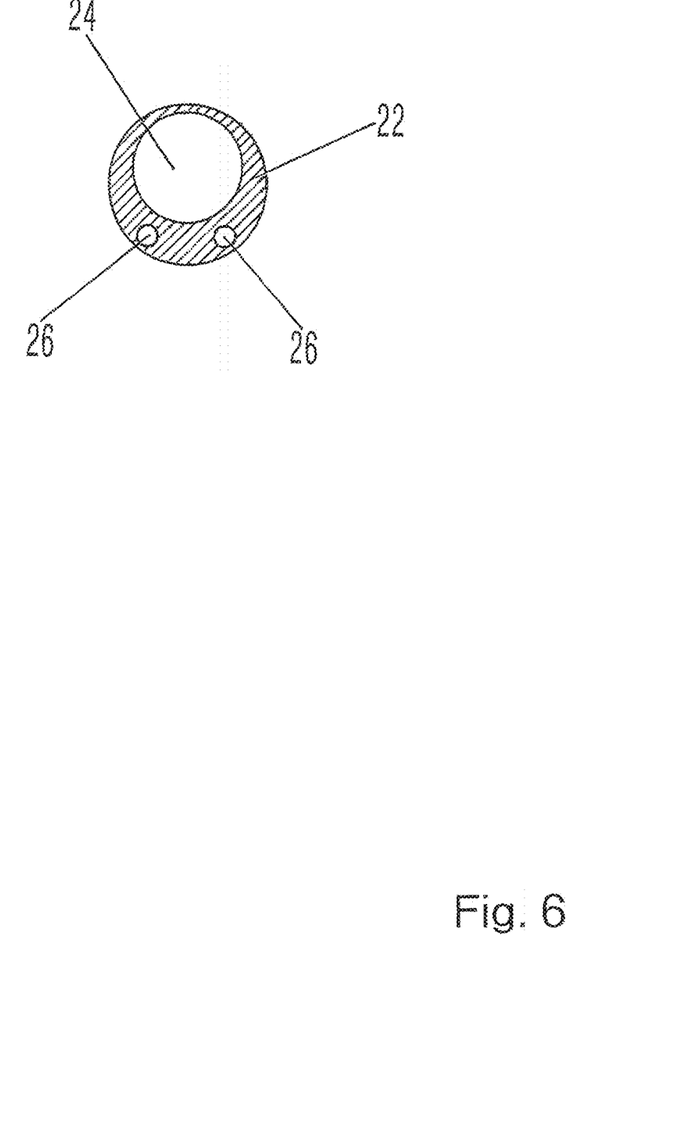
Figure 7:
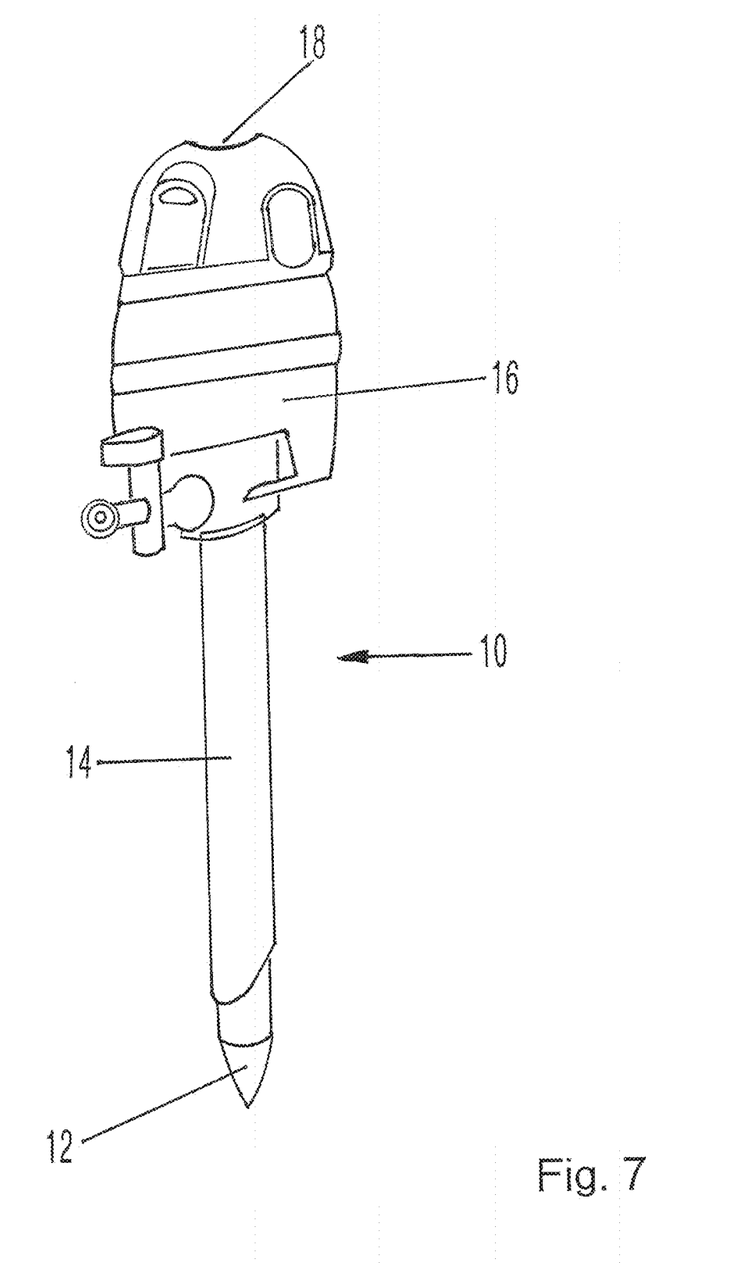

FIG. 7 shows an example of a conventionally, already known trocar such as can be used within the framework of the present disclosure. The trocar 10 has a trocar mandrel 12, which is also known as an obturator. The trocar mandrel 12 is inserted coaxially in a trocar sleeve 14. The distal tip of the trocar mandrel 12 projects distally out of the trocar sleeve 14. A valve block 16 is disposed at the proximal end of the trocar sleeve 14. A valve in the valve block 16 closes off the proximal end of the trocar sleeve 14 when no trocar mandrel 12 is used. The valve block 16 allows for sealed introduction of the trocar mandrel 12 or of surgical instruments. The trocar 10 is preferably designed as an optical trocar, in which at least the distal tip of the trocar mandrel 12 is transparent and can be observed through an optical system, which can be introduced into the hollow trocar mandrel 12 through the proximal opening 18. According to the invention present disclosure, any other commercially available trocars may be used instead of the trocar 10 shown in FIG. 7.

In order to be able to perform preoperative or surgical procedures in front of the distal tip of the trocar 10 upon insertion of the trocar 10, according to the present disclosure a working sleeve 20 is used, as is shown in a first embodiment in FIGS. 1 to 6.

The working sleeve 20, which preferably consists of plastic, has a tubular shaft 22, through which a continuous inner channel 24 passes axially. The length of the tubular shaft 22 and the inner channel 24 from the open proximal end of the inner channel 24 to the open distal end of the inner channel 24 corresponds to the length of the trocar 10 or the trocar sleeve 14 in front of the valve block 16. The open inner diameter of the inner channel 24 corresponds to the outer diameter of the trocar sleeve 14. The length of the tubular shaft 22 and the inner diameter of the inner channel 24 in various sizes of the working sleeve 20 are adapted to the standardized lengths and diameters of the commercially available trocars 10.

In the tubing wall of the tubular shaft 22, at least one working channel 26 extends, axially parallel to the inner channel 24. Two working channels 26 are provided in the embodiment shown. The working channels 26 serve for the introduction of miniature instruments, known in and of themselves. For example, such miniature instruments may be forceps, scissors, clamps, coagulators, ultrasonic dissectors, etc.

At the proximal end of the tubular shaft 22, the working sleeve 20 expands into a cage 28 made in one piece with the tubular shaft 22. The cage 28 is formed by two brackets 30 located diametrically opposite one another with regard to the middle axis of the tubular shaft 22. The brackets 30 extend in the proximal direction from the bottom 32 into which the open proximal end of the inner channel 24 opens and are curved outward relative to the central axis, as is most clearly apparent in FIG. 3. The proximal free ends of the brackets 30 are connected together by a rim 34 in the form of a semicircle, which travels in a plane perpendicular to the middle axis of the working sleeve 20. The cage 28 thus surrounds a proximally open accommodation chamber, the internal dimensions of which are adapted to the dimensions of the valve block 16. Preferably means are provided in the cage 28 for retaining the valve block 16 in the cage 28 when the trocar 10 is inserted. In this way rotation or axial shifting between the working sleeve 20 and the trocar 10 can be avoided. Such retaining means can for example be retaining clips 46, plastic lugs or the like formed on the inside of the cage 28, which firmly clamp the valve block 16 or retain it elastically in the cage 28.

The working channels 26 pass continuously in an axial direction through the entire working sleeve 20. In the embodiment shown with two working channels 26, each of the working channels 26 starts with an open proximal inlet opening 36 in the proximal end face of the respective bracket 30. The working channels 26 extend from the proximal inlet opening 36 into the respective bracket 30, then pass into the tubular wall of the tubular shaft 22, extend parallel to the axis into the inner channel 24 through the tubular shaft 22, and open at the distal end into an open distal outlet opening 38 in the distal front face of the tubular shaft 22. The tubular shaft 22 is preferably conical at the distal end to prevent a difference in height from the trocar sleeve 14 to the work in sleeve 20, which could cause a change in the penetration pressure during insertion.

In the working channels 26, mandrels may preferably be used that are introduced into the working channels 26 from the proximal end. When the mandrel is inserted, this blocks the corresponding distal outlet opening 38 in each case and also fits flush into the outer contour of the working sleeve 20. This makes it possible to avoid entry of tissue into the working channel 26 during the insertion of the trocar 10 with the working sleeve 20.

A Radially outward projecting appendage 40 is molded onto the outer perimeter of the rim 34 and is preferably provided with threading. The appendage 40 serves as the means for fixing the working sleeve 20, for example, to an arm of a stand or another positioning and retaining system.

The trocar system according to the invention present disclosure is used as follows.

The trocar 10 with trocar mandrel 12 and trocar sleeve 14 is inserted in the working sleeve 20. For this purpose the trocar 10 is inserted by its distal end into the open proximal end of the inner channel 24 until the valve block 16 is enclosed in the cage 28, strikes the bottom of the cage 28 and is arrested in the cage 32. The distal tip of the trocar 10, especially the distal tip of the trocar mandrel 12, now projects distally out of the distal end of the working sleeve 20. A seal 42 disposed in the proximal end of the inner channel 24, for example a lip seal made of a flexible plastic, is adjacent to the outer perimeter of the trocar sleeve 14 and thus seals the trocar 10 in the working sleeve 20. The trocar 10 with the working sleeve 20 can now be made to pierce the tissue of the patient, for example in the abdominal wall, wherein preferably the advancement of the trocar tip can be observed with an optical system introduced into the trocar mandrel 12.

Miniature instruments 50 can be introduced into the working channel 26 in this way. These miniature instruments 50 frequently have a flexible shaft, so that they can be introduced even into curved working channels 26. These miniature instruments 50 are introduced into the proximal inlet opening 36 of the working channel 26 until the distal working elements 52 of the miniature instruments 50 emerge from the outlet opening 38 of the respective working channel 26 and extend in front of the distal tip of the tracer 10. The operating hand grip of the miniature instruments 50 remains in the proximal area outside of the working channel 26. In the proximal inlet opening 36 of the working channel 26, preferably there is also a seal 44, e.g., a combination of a lip seal and a flap seal made of plastic, provided to seal the miniature instruments in the working channels 26 and to close the work in channels when no miniature instrument 50 is inserted.

Using the miniature instruments 50 passed through the working channels 26 in front of the distal tip of the trocar 10, preparative steps can be performed to facilitate the penetration of the trocar 10 and, for example, to allow the cutting of resistant tissue layers. It is also possible using the miniature instruments introduced to perform surgical procedures in the desired surgical field, wherein the surgical steps can be performed under visual observation, either by observing the surgical field through the transparent tip of the optical trocar or in that the trocar mandrel 12 is withdrawn from the tracer sleeve 14 and replaced by an optical system. If the tracer mandrel 12 is replaced by an optical system, this optical system can preferably be fixed in the tracer sleeve 14 by suitable means. Such means can be formed on the trocar sleeve 14, especially on the valve block 16 or on the cage 28. When the tracer 10 with the working sleeve 20 is brought into the desired position, the working sleeve 20 can be fixed in its position using the appendage 40, as a result of which the tracer 10 retained in the working sleeve 20 is also held and fixed in its position. This fixation facilitates the surgical procedure.

Figure 8:
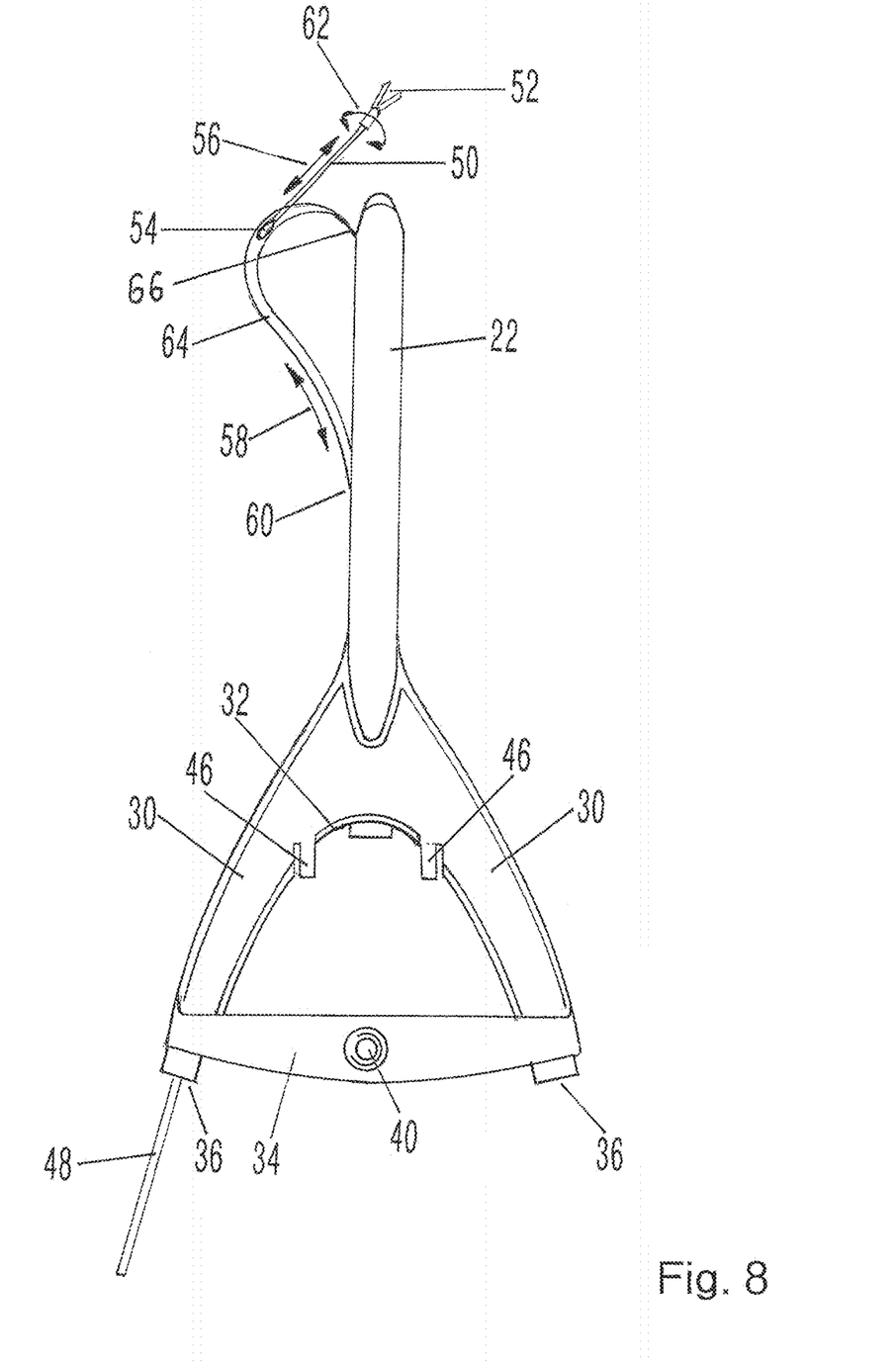

In an additional embodiment of the present disclosure shown in FIG. 8, the at least one working channel is formed with a flexible guiding channel 48. The guiding channel 48, preferably made of plastic, is movably guided in the longitudinal direction along the working sleeve (22). For this purpose, for example, the guiding channel 48 is introduced through the proximal inlet opening 36 and extends in the bracket 30 and the tubular shaft 23 to an outlet opening 60, through the which the guiding channel 48 emerges laterally from the tubular shaft 22. The distal end 66 of the flexible guiding channel 48 is fixed on the distal end of the tubular shaft 22. If the flexible guiding channel is advanced distally in the working sleeve 22, the longitudinal region 64 of the guiding channel 48 between the outlet opening 60 and the fixation of the distal end 66 is curved laterally away from the tubular shaft 22 toward the outside and curved outward in the distal direction, as is seen in FIG. 8. In the outwardly bowing distal longitudinal region 64 of the guiding channel 48, the distal outlet opening 54 for an introduced miniature instrument 50 is formed. If the miniature instrument 50 is introduced from the proximal end into the guiding channel 48, the miniature instrument 50 with its distal working element 52 emerges through this outlet opening 54 and is guided in front of the distal tip of the working sleeve 20 or the trocar 10 inserted in the working sleeve 20.

As is shown in FIG. 8, by means of a longitudinal displacement of the guiding channel 48, as indicated by the arrow 58, the outward curvature of the distal longitudinal region 64 of the guiding channel 48 can be controlled. As a result of the differential curvature, the outlet opening 54 reaches a different curvature region of the protruding longitudinal region 64. As a result, the angle of emergence of the miniature instrument 50 from the guiding channel 48 is influenced adjustably. By longitudinal displacement of the miniature instrument 50 in the guiding channel 48, in addition, the length of emergence of the distal end of the miniature instrument 50 can be selected adjustably, as is indicated by the arrow 56. By adjusting the outlet angle and the outlet length, the working element 52 of the miniature instrument 50 can be positioned in space in front of the distal tip of the working sleeve 20. Finally the miniature instrument 50 can be rotated in the guiding channel 48, whereby the working element 52 can be rotated around the longitudinal axis of the miniature instrument 50, as is indicated by the arrow 62. This makes it possible, for example, to rotate the cutting plane of a working element 52.

Additional details of the design of the working channels as flexible guiding channels are described in DE 10 2012 303 908 B3, which is incorporated by reference in its entirety.

LIST OF SYMBOLS

10 Trocar
12 Trocar mandrel
14 Trocar sleeve
16 Valve block
18 Opening
20 Working sleeve
22 Tubular shaft
24 Inner channel
26 Working channel
28 Cage
30 Bracket
32 Base
34 Rim
36 Proximal inlet opening
38 Distal outlet opening
40 Appendage
42 Seal
44 Seal
46 Retaining clips
48 Guiding channel
50 Miniature instrument
52 Working element
54 Outlet opening
56 Adjustment of the emergence distance
58 Adjustment of the emergence angle
60 Outlet opening
62 Rotation of the working element
64 Length range
66 Distal end of 48

The invention claimed is:

1. A trocar system, comprising:
a trocar with a trocar mandrel having a distal tip, a trocar sleeve with a trocar sleeve outer periphery, and a valve block,
a tubular working sleeve with an axially continuous inner channel configured to receive the trocar such that the trocar sleeve is sealed along the trocar sleeve outer periphery in the inner channel,
wherein the distal tip of the trocar mandrel emerges distally from the working sleeve,
wherein the valve block is located outside of the inner channel,
wherein a working channel is formed in the working sleeve that extends from a proximal inlet opening to a distal outlet opening,
wherein the working channel is formed with a flexible guiding channel, which is guided movably along the working sleeve in a longitudinal direction,
wherein a distal end of the guiding channel is fixed distally on the working sleeve, so that during advancement of the guiding channel along with working sleeve the guiding channel bends laterally away from the working sleeve, and
wherein a distal outlet opening is located laterally in a wall of the guiding channel in an outwardly bendable distal region thereof.

2. The trocar system according to claim 1, wherein the working channel is arranged in a tubular wall of the working sleeve and the working channel is continuous.

3. The trocar system according to claim 2, wherein a distal opening of the working channel opens into a distal front face of the tubular wall of the working sleeve.

4. The trocar system according to claim 1, further comprising a seal arranged in a proximal end of the inner channel, wherein the seal abuts the trocar sleeve in a sealing manner when the trocar is inserted.

5. The trocar system according to claim 1, further comprising a seal at the proximal inlet opening of the working channel.

6. The trocar system according to claim 1, wherein a proximal end of the working sleeve is formed as a cage, which when the trocar is inserted accommodates the valve block, wherein the cage is expanded proximally and open proximally, wherein an open proximal end of the inner channel opens in a distal-side base of the cage, and wherein the proximal inlet opening of the working channel opens into a proximal-end rim of the cage.

7. The trocar system according to claim 6, wherein the cage has two diametrically arranged brackets, which extend proximally from a bottom of the cage and extend outward in a curved shape, wherein a proximal end of the two diametrically arranged brackets are connected by a proximal side rim of the cage, and wherein the working channel extends in at least one of the diametrically arranged brackets.

8. The trocar system according to claim 7, further comprising an appendage of the proximal-side rim of the cage for fixing the trocar system.

9. The trocar system according to claim 8, wherein the appendage extends radially outward from the proximal-side rim.

10. The trocar system according to claim 6, further comprising a clamp on the cage that retains the trocar or the valve block.

11. The trocar system according to claim 1, further comprising an appendage on a cage of the working sleeve or on the valve block of the trocar that secures an optical system inserted in the trocar sleeve.

12. A trocar system, comprising: a trocar with a trocar mandrel having a distal tip, a trocar sleeve with a trocar sleeve outer periphery, and a valve block, a tubular working sleeve with an axially continuous inner channel configured to receive the trocar such that the trocar sleeve is sealed along the trocar sleeve outer periphery in the inner channel, wherein the distal tip of the trocar mandrel emerges distally from the working sleeve, wherein the valve block emerges distally from the working sleeve and the valve block is located proximally outside of the inner channel, wherein a working channel formed in the working sleeve that extends from a proximal inlet opening to a distal outlet opening, wherein an proximal end of the working sleeve is formed as a cage, which when the trocar is inserted accommodates the valve block, wherein the cage is expanded proximally and open proximally, wherein an open proximal end of the inner channel opens in a distal-side base of the cage, and wherein the proximal inlet opening of the working channel opens into a proximal-end rim of the cage.

13. The trocar system according to claim 12, wherein the working channel is formed with a flexible guiding channel, which is guided movably along the working sleeve in a longitudinal direction, wherein a distal end of the guiding channel is fixed distally on the working sleeve, so that during advancement of the guiding channel along with working sleeve the guiding channel bends laterally away from the working sleeve, and wherein a distal outlet opening is located laterally in a wall of the guiding channel in an outwardly bendable distal region thereof.

14. The trocar system according to claim 12, wherein the working channel is arranged in a tubular wall of the working sleeve and the working channel is continuous, and wherein a distal opening of the working channel opens into a distal front face of the tubular wall of the working sleeve.

15. The trocar system according to claim 12, further comprising a seal arranged in a proximal end of the inner channel, wherein the seal abuts the trocar sleeve in a sealing manner when the trocar is inserted.

16. The trocar system according to claim 12, further comprising a seal at the proximal inlet opening of the working channel.

17. The trocar system according to claim 12, wherein the cage has two diametrically arranged brackets, which extend proximally from a bottom of the cage and extend outward in a curved shape, wherein a proximal end of the two diametrically arranged brackets are connected by a proximal side rim of the cage, and wherein the working channel extends in at least one of the diametrically arranged brackets.

18. The trocar system according to claim 17, further comprising an appendage of the proximal-side rim of the cage for fixing the trocar system.

19. The trocar system according to claim 18, wherein the appendage extends radially outward from the proximal-side rim.

20. The trocar system according to claim 12, further comprising a clamp on the cage that retains the trocar or the valve block.

* * * * *